(12) United States Patent
Gupta et al.

(10) Patent No.: US 7,040,141 B2
(45) Date of Patent: May 9, 2006

(54) CAPILLARY CONDENSATION METHOD AND APPARATUS FOR DETERMINING POROSITY CHARACTERISTICS OF A SAMPLE

(75) Inventors: Krishna M. Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 22 days.

(21) Appl. No.: 10/419,393

(22) Filed: Apr. 21, 2003

(65) Prior Publication Data

US 2004/0206160 A1    Oct. 21, 2004

(51) Int. Cl.
*G01N 15/08* (2006.01)

(52) U.S. Cl. .......................................... 73/38
(58) Field of Classification Search ............ 73/38
See application file for complete search history.

(56) References Cited

U.S. PATENT DOCUMENTS

| | | | |
|---|---|---|---|
| 2,465,948 A | 3/1949 | Welge | |
| 2,534,737 A | 12/1950 | Rose | |
| 2,612,036 A | 9/1952 | Angona | |
| 2,709,904 A | 4/1955 | Hertel | |
| 2,755,660 A | 7/1956 | Kammermeyer et al. | |
| 3,286,509 A * | 11/1966 | Gluckman et al. | 73/38 |
| 3,548,634 A * | 12/1970 | Roy | 73/38 |
| 3,590,634 A * | 7/1971 | Pasternak et al. | 73/38 |
| 4,203,317 A | 5/1980 | Gupta | |
| 4,217,336 A | 8/1980 | Maire et al. | |
| 4,576,927 A | 3/1986 | Kuroda et al. | |
| 4,656,865 A * | 4/1987 | Callan | 73/38 |
| 4,660,412 A | 4/1987 | Gupta | |
| 4,744,240 A | 5/1988 | Reichelt | |
| 5,245,859 A * | 9/1993 | Smith et al. | 73/38 |
| 5,695,818 A | 12/1997 | Soffer et al. | |
| 5,696,198 A | 12/1997 | Chereisky et al. | |

(Continued)

FOREIGN PATENT DOCUMENTS

| | | |
|---|---|---|
| EP | 0139202 | 5/1985 |
| EP | 0831318 | 3/1998 |

(Continued)

OTHER PUBLICATIONS

Jena, Akshaya K. and Gupta, Krishna M.. "In-Plane Compression Porometry of Battery Separators." Journal of Power Sources 80. 1999. p. 46-52.

(Continued)

*Primary Examiner*—Hezron Williams
*Assistant Examiner*—Ryan Christensen
(74) *Attorney, Agent, or Firm*—Brown & Michaels, PC

(57) ABSTRACT

A sample having a plurality of pores is located within a pressurizable chamber. The sample divides the chamber into a first volume and a second volume. A known amount of vapor is introduced into the first volume and the second volume at the same pressure ($P_x$). After equilibrium is reached, pressure and decrease in volume of vapor are measured. Pore diameter and pore volume are calculated. A pressure differential is created between the two volumes, and the pressure change is monitored after the pressure differential is introduced. In a preferred embodiment, the pressure is increased in the first volume by a small percentage ($\Delta P_x$), and the pressure change on both sides of the sample is monitored after the pressure increase. The flow rate of the vapor is calculated using the pressure change. These steps are preferably repeated. The pore distribution in the sample is preferably calculated from the flow rates.

17 Claims, 3 Drawing Sheets

U.S. PATENT DOCUMENTS

| | | | |
|---|---|---|---|
| 5,955,185 | A | 9/1999 | Yoshino et al. |
| 6,119,506 | A * | 9/2000 | Gibson et al. ................. 73/38 |

FOREIGN PATENT DOCUMENTS

| | | |
|---|---|---|
| RU | 1807341 | 4/1993 |
| SU | 229002 | 2/1969 |
| SU | 853492 | 8/1981 |
| SU | 1118900 | 10/1984 |
| SU | 1130772 | 12/1984 |

OTHER PUBLICATIONS

Gupta, Vibhor and Jena, A.K.. "Substitution of Alcohol in Porometers For Bubble Point Determination." Advances in Filtration and Separation Technology. Col. 13b, 1999 p. 833-844.

Gupta, Nalini and Jena, Akshaya. "Measuring in Layers: Determining the Pore Structure of Individual Layers of Multi-Layered Ceramic Composites." Ceramic Industry, Feb. 2001. p. 28-33.

Jena, Akshaya K. and Gupta, Krishna M. "Detemination of Pore Volume and Pore Distribution by Liquid Extrusion Porosimetry Without Using Mercury" Ceramic Engineering and Science Proceedings, 2002, p. 277-284.

Thelen, E. "Soil Permeability Tester", Franklin Institute Laboratories Notes: Franklin Inst. Journal, vol. 253, Apr. 1952, pp. 340-341.

"DWI-LB74 Porosity" http://www.dwi.twth-aachen.de/lb/74.html. Dec. 27, 1997.

Jena, Akshaya K. and Gupta, Krishna M. "A Novel Mercury Free Technique for Determination of Pore Volume, Pore Size and Liquid Permeability." P/M Science & Technology Briefs, vol. 4, No. 1, 2002. pp. 5-8.

Jena, Akshaya K. and Gupta, Krishna M. "Materials Pore-Sight Testing Pore Volume and Flow Through Porous Materials" Materials World, The Journal of the Institute of Materials, vol. 10, Num. 2, Feb. 2002.

* cited by examiner

CAPILLARY CONDENSATION METHOD AND APPARATUS FOR DETERMINING POROSITY CHARACTERISTICS OF A SAMPLE

BACKGROUND OF THE INVENTION

1. Field of the Invention

The invention pertains to the field of porosimetery, or the measurement of the porosity of substances. More particularly, the invention pertains to a capillary condensation method and apparatus for determining the porosity characteristics of a sample.

2. Description of Related Art

FIG. 1 shows a graph (10) of the gas flow through a sample with a plurality of pores as the pressure is increased. When the sample is dry (11), all of the pores are empty, so the gas flows proportionally to the amount of pressure being added. After wetting the sample, the pores are all filled (12) with the wetting fluid. Therefore, the gas does not flow through the blocked pores. However, as the pressure increases, the bubble point (13) of the largest pores is reached. The pores empty out (15) as their bubble points are reached. The pressure continues to increase, until all of the pores have been emptied (14). The pore distribution of the sample is calculated using the ratio between the wet and dry flow measurements.

The bubble point of a pore in a sample is pressure that can overcome the capillary action of the fluid within the pores. The size of the pores in a material determines the bubble points, or the pressure at which the liquid is extruded or forced out of the pores—the bubble points are inversely proportional to the size of the pores. Therefore smaller pores require higher pressure to reach their bubble point. However, higher pressure can damage the sample material.

Therefore, for a sample with small pores, an alternative method can be used. A vapor added to the sample chamber can condense in the pores, block the pores, and decrease the flow rate of the gas. At a very low pressure, the vapor flows through all the pores. As the pressure increases, vapor condenses in the smallest pores first and decreases the flow rate of the gas. As vapor pressure increases, the permeability also decreases. If the permeability at different pressures is known, the pore distribution can be calculated. A much smaller pressure is required in this method than in the liquid extrusion method described above. Much smaller pores can also be measured by this technique. It is also possible to measure pore volume by this method by measuring the amount of condensed vapor. The extrusion technique cannot measure pore volume.

SUMMARY OF THE INVENTION

A method and apparatus for determining the porosity characteristics of a sample having a plurality of pores is disclosed. The sample is located within a pressurizable chamber and the sample divides the chamber into a first volume and a second volume. The method begins by introducing a known amount of vapor into the first volume and the second volume at the same pressure. In a preferred embodiment, the pore diameter is calculated after measuring a decreased final pressure in the chamber after equilibrium is reached. In another preferred embodiment, a decrease in the amount of vapor in the chamber is used to calculate pore volume.

A pressure differential is created, preferably by increasing the pressure in the first volume by a small percentage ($\Delta P_x$), and the pressure change on both sides of the sample is monitored over time. The flow rate of the vapor is calculated using the pressure change. These steps are preferably repeated. The pore distribution in the sample given in terms of distribution of flow over pore diameter is preferably calculated from the flow rates. Thus, pore diameter, pore volume and flow distribution are measurable by this invention.

DETAILED DESCRIPTION OF THE INVENTION

Figure 1:
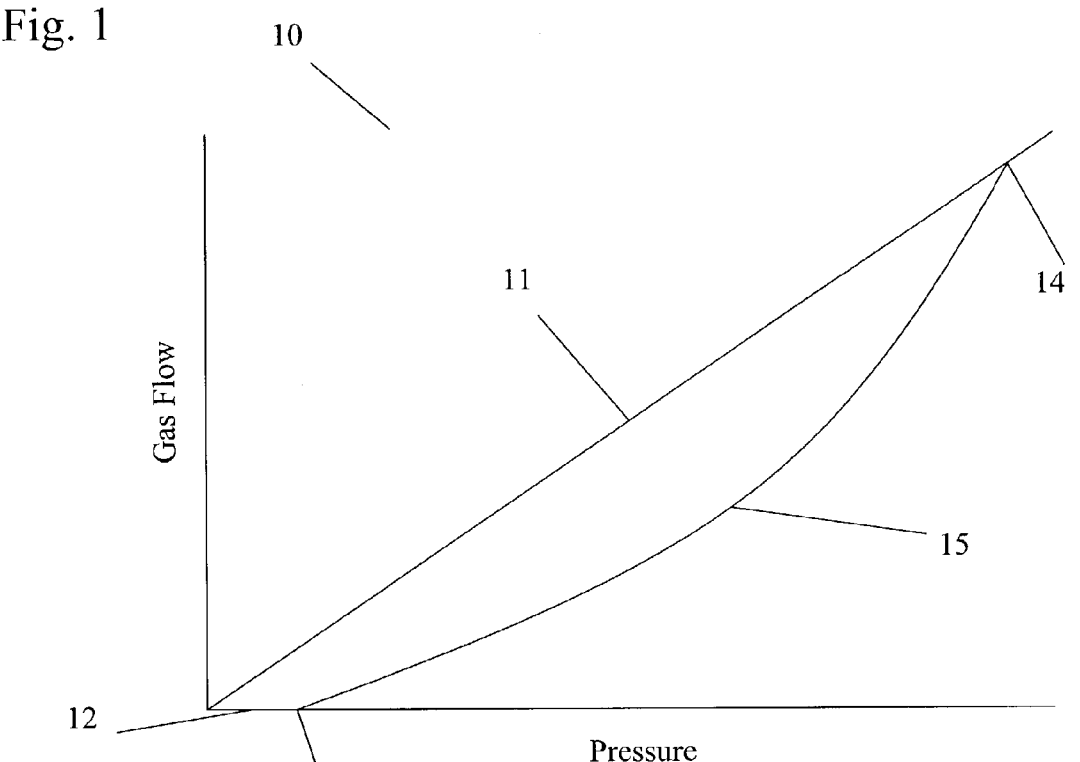
FIG. 1 shows a graph of gas flow through a sample with an increase in pressure in a dry sample and a wetted sample.
Figure 2:
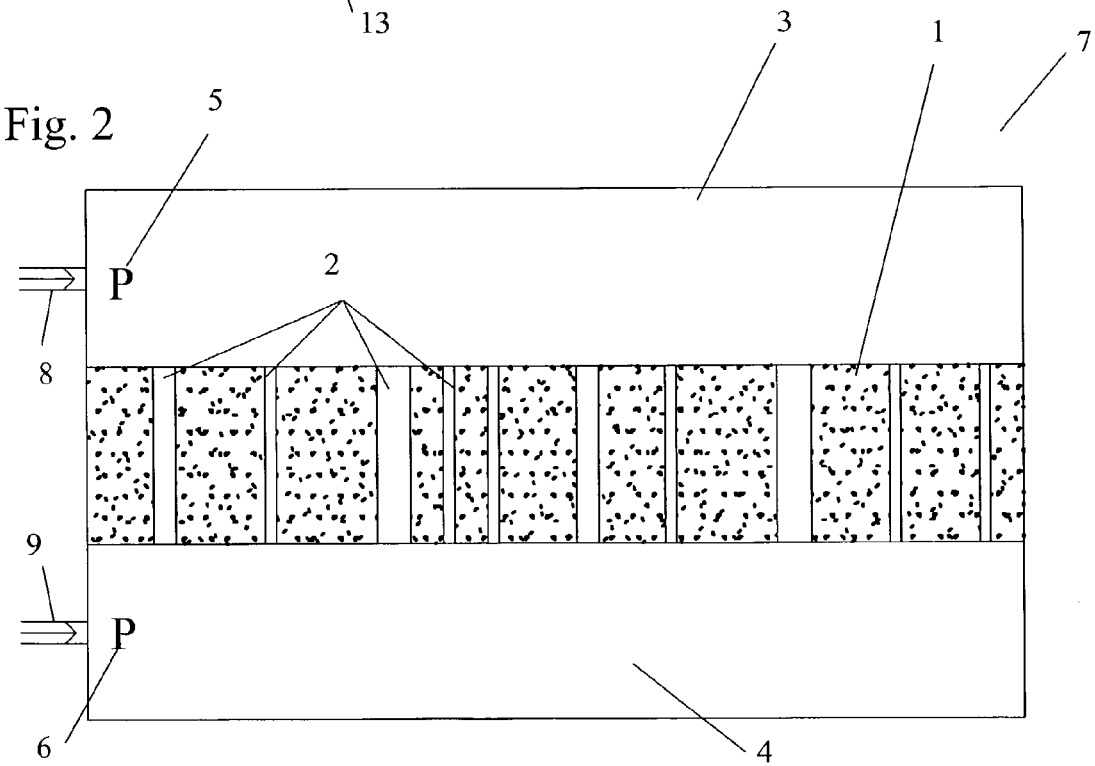
FIG. 2 shows an apparatus in an embodiment of the present invention.

Referring now to FIG. 2, the apparatus of the present invention includes a pressurizable chamber (7) for holding a sample (1). The sample (1), which has a plurality of pores (2), divides the single chamber (7) into two volumes (3) and (4) flanking the sample (1). O-ring seals are preferably used to prevent leakage around the sample.

The sample (1) divides the chamber (7) into a first volume (3) on a first side of the sample (1) and a second volume (4) on a second side of the sample (1). In the example shown in FIG. 2, the first volume (3) is above the sample (1) and the second volume (4) is below the sample (1). Vapor at a certain pressure (5) and (6) can be introduced through pressure inlets (8) and (9), respectively, into the volume (3) above the sample (1) and the volume (4) below the sample (1).

Figure 3:
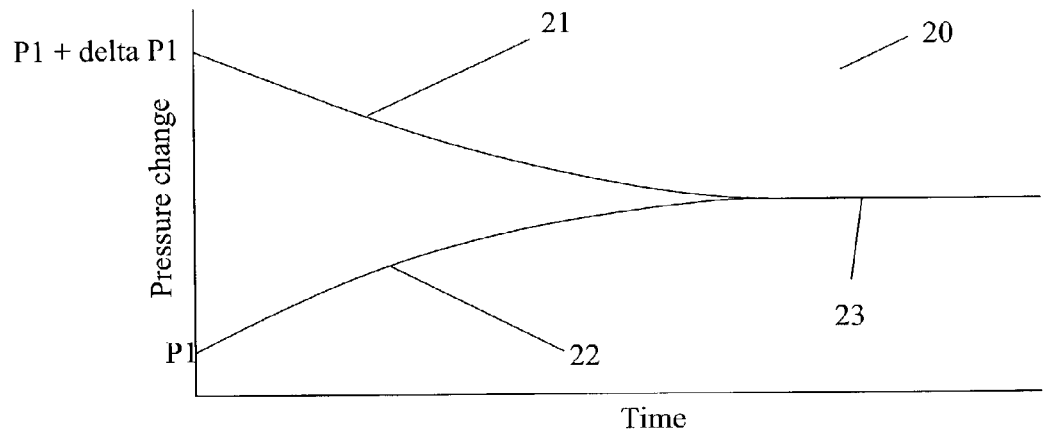
FIG. 3 shows a graph of the result of a change in the pressure in both sides of the sample in an embodiment of the present invention.
Figure 4:
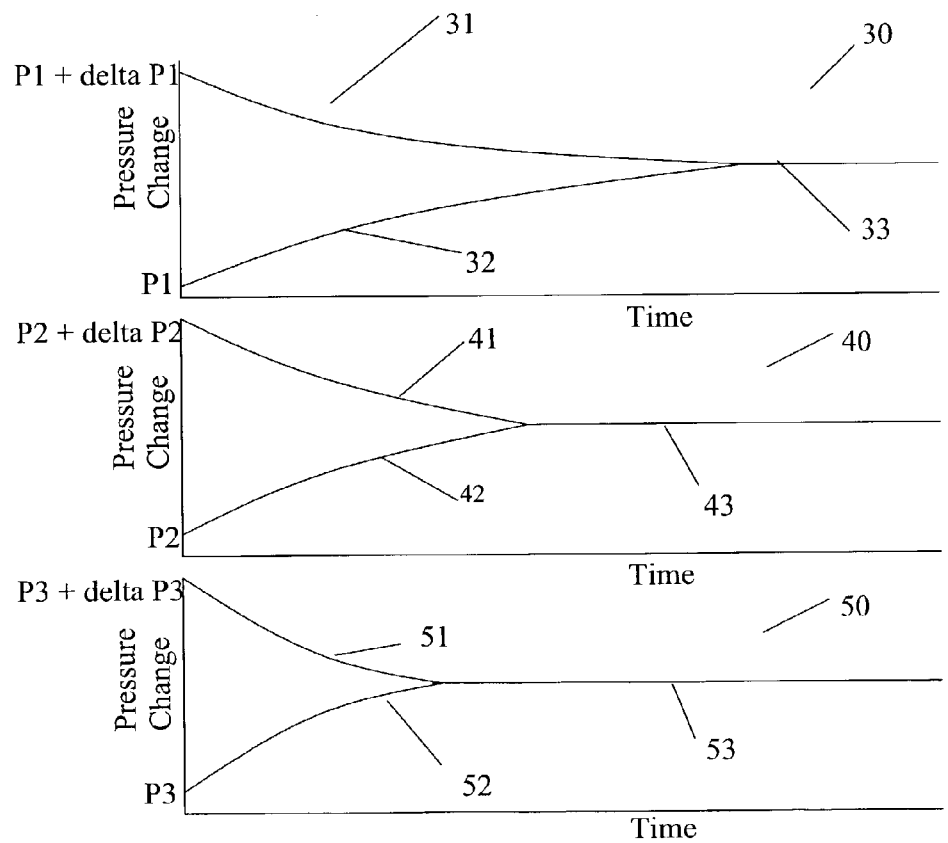
FIG. 4 shows a graph of the result of multiple changes in pressure in both sides of the sample in an embodiment of the present invention.
Figure 5:
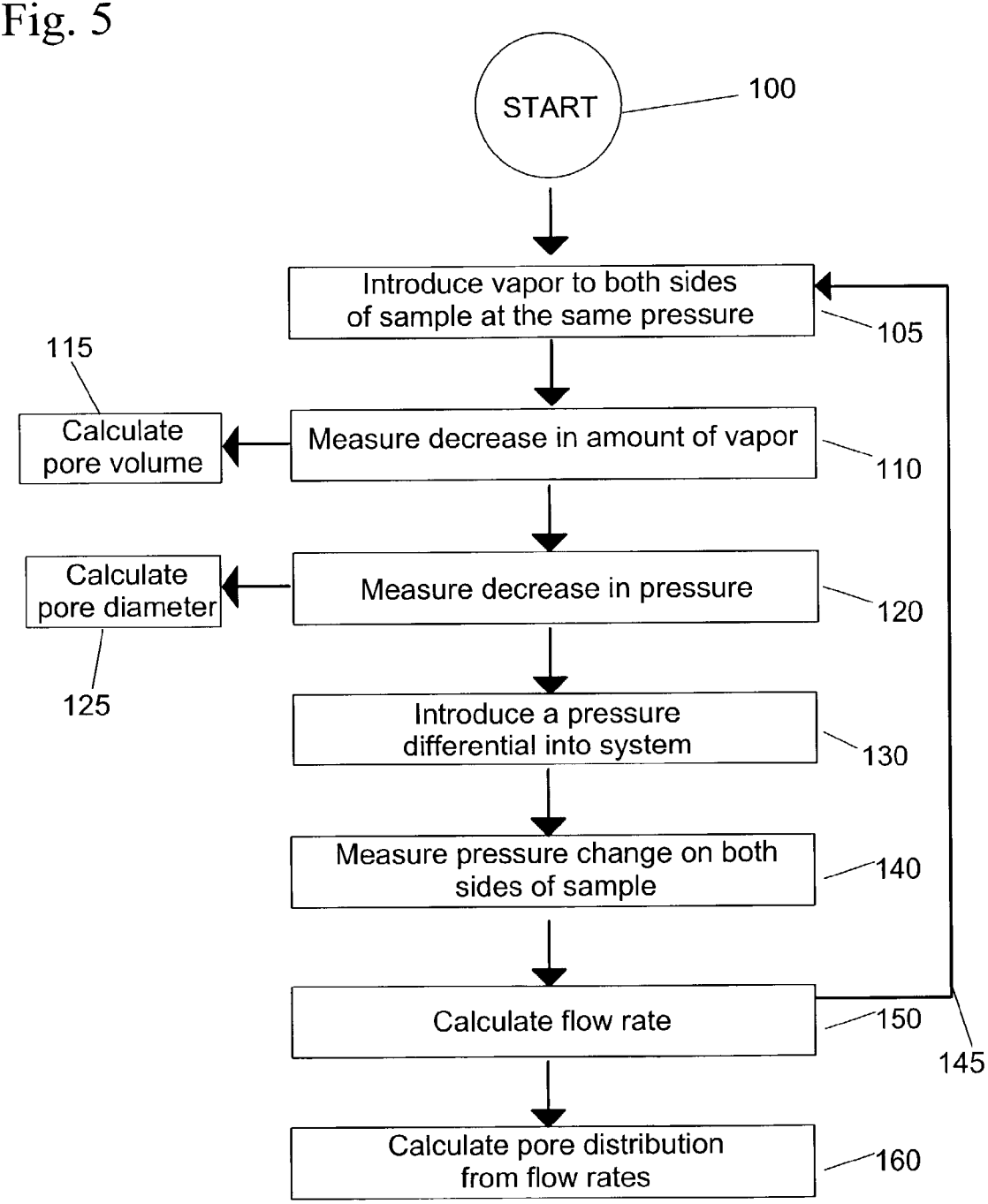
FIG. 5 shows a flowchart of a method of the present invention.

Referring now to FIGS. 3–5, the method of the present invention starts in step (100) with a sample (1) in the chamber (7). By opening valves, a known amount of vapor contained in a known volume at known pressure is introduced into both volumes (3) and (4) at the same pressure (5) and (6) through pressure inlets (8) and (9) in step (105).

The decrease in the amount of vapor after it is added is measured in step (110). This measurement is preferably used to calculate the pore volume of the sample (1) in step (115). The amount of the final pressure is measured in step (120). This measurement is preferably used to calculate the pore diameter of the sample (1) in step (125).

A pressure differential between the first volume (3) and the second volume (4) is introduced into the system in step (130). For example, the pressure in one volume (3) is increased by a small percentage by introducing vapor into this volume through the appropriate valve. In a preferred embodiment, the increase in pressure is approximately 1%. The new pressure is $P_x + \Delta P_x$. Although the pressure increase ($\Delta P_x$) is described on volume (3) in the examples, the pressure increase ($\Delta P_x$) could alternatively be increased on volume (4) or decreased in one of the volumes.

After this step, the pressure on both sides changes in response to the pressure differential on the two sides of the sample. The pressure change is monitored, and shown schematically in FIGS. 3 and 4.

In this example, the pressure decrease (21) on side (3) after $P_1 + \Delta P_1$ is added to that side (3), is symmetrical with the corresponding pressure increase (22) on the other side (4). The pressure, $P_x$ gives the largest of the size of the pores, that contain liquid and do not permit gas flow at $P_x$. The rate of change in the pressure gives the flow rate. Pressure (21) decreases and the pressure (22) increases, until both sides reach an equilibrium (23).

The pressure change on both sides of the sample (1) is measured in step (140). The flow rate is calculated from the pressure change in step (150). Steps (105) through (150) are preferably repeated multiple times at a higher pressure in step (145). In a preferred embodiment, these steps are repeated twenty to thirty times.

In the example, each time the pressure on side (3) is increased by $\Delta P_x$, the subsequent pressure decrease (31), (41), and (51) on side (3) is symmetrical with the corresponding pressure increase (32), (42), and (52) on side (4). The pressure on both sides eventually meet at an equilibrium point (33), (43), and (53).

The pore distribution is calculated from the flow rates in step (160). The rate of change of pressure gives the flow rate per unit pressure difference across the sample through pores larger than those containing liquid due to condensation at the measurement pressure. Variation of flow rate per unit pressure difference with pore diameter yields cumulative flow distribution. These data yield distribution of flow rate over pore diameter, which is the same pore distribution measured by extrusion flow porometry.

Although the prior art gas adsorption technique that operates at liquid nitrogen temperatures can also measure pore volume, the extreme temperatures make it expensive and difficult to implement. In contrast, the present invention overcomes these shortcomings by using temperatures closer to room temperature. The present invention also can measure pore characteristics not measurable by the gas adsorption technique.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of determining the porosity characteristics of a sample having a plurality of pores, wherein the sample is located within a pressurizable sample chamber, and the sample divides the chamber into a first volume and a second volume, comprising the steps of:
   a) introducing a known amount of vapor into the first volume and the second volume at the same pressure;
   b) creating a pressure differential between the first volume and the second volume; and
   c) monitoring a decrease over time in the pressure differential, created in step b), between the first and second volumes as pressure in the first volume and pressure in the second volume approach an equilibrium point.

2. The method of claim 1, further comprising, after step (a), the step of calculating pore diameter, comprising the substeps of:
   i) measuring the pressure in the chamber after the chamber reaches equilibrium; and
   ii) calculating a pore diameter using the measurement from substep (i).

3. The method of claim 1, wherein step (b) is performed by introducing additional vapor into the first volume to increase the pressure in the first volume by a small amount.

4. The method of claim 1, further comprising the step of:
   d) calculating a flow rate of the vapor using the rate of pressure differential change in step (c).

5. The method of claim 4, further comprising the step of:
   e) repeating steps (a) through (d) at a different pressure.

6. The method of claim 5, further comprising the step of:
   f) calculating a pore distribution of the pores in the sample from the flow rates.

7. The method of claim 1, further comprising, after step (a), the step of calculating pore volume, comprising the substeps of:
   i) measuring an amount of vapor in the chamber after the chamber reaches equilibrium; and
   ii) calculating a pore volume using the measurement from substep (i).

8. The method of claim 1, wherein the porosity characteristics being determined are selected from the group consisting of pore volume and pore diameter.

9. The method of claim 1, wherein the porosity characteristic being determined is selected from the group consisting of flow rate and pore distribution.

10. A method of determining the porosity characteristics of a sample having a plurality of pores, wherein the sample is located within a pressurizable sample chamber, and the sample divides the chamber into a first volume and a second volume, comprising the steps of:
   a) introducing a known amount of vapor into the first volume and the second volume at the same pressure;
   b) creating a pressure differential between the first volume and the second volume;
   c) monitoring a decrease over time in the pressure differential between the first and second volumes as pressure in the first volume and pressure in the second volume approach an equilibrium point; and
   d) calculating a flow rate of the vapor using the rate of pressure differential change in step (c).

11. The method of claim 10, further comprising the step of:
   e) repeating steps (a) through (d) at a different pressure.

12. The method of claim 11, further comprising the step of:
   f) calculating a pore distribution of the pores in the sample from the flow rates.

13. The method of claim 11, wherein step (b) is performed by introducing additional vapor into the first volume to increase the pressure in the first volume by a small amount.

14. A method of determining the porosity characteristics of a sample having a plurality of pores, wherein the sample is located within a pressurizable sample chamber, and the sample divides the chamber into a first volume and a second volume, comprising the steps of:
   a) introducing a known amount of vapor into the first volume and the second volume at the same pressure;
   b) creating a pressure differential between the first volume and the second volume;
   c) monitoring a decrease over time in the pressure differential between the first and second volumes as pressure in the first volume and pressure in the second volume approach an equilibrium point; and
   d) calculating pore volume, comprising the substeps of:
      i) measuring an amount of vapor in the chamber after the chamber reaches equilibrium; and
      ii) calculating a pore volume using the measurement from substep (i).

15. The method of claim 14, wherein step (b) is performed by introducing additional vapor into the first volume to increase the pressure in the first volume by a small amount.

16. The method of claim 3, wherein the pressure in the first volume is increased by approximately one percent.

17. The method of claim 1, wherein step b) comprises the substep of decreasing the pressure in the first volume.

* * * * *